(12) United States Patent
Germanier

(10) Patent No.: US 6,997,707 B2
(45) Date of Patent: Feb. 14, 2006

(54) POSITIONING DEVICE FOR FITTING IMPLANT-SUPPORTED DENTAL PROSTHESES

(76) Inventor: Yves Germanier, 27, Ouai du Mont-Blanc, CH-1201, Geneve (CH)

( * ) Notice: Subject to any disclaimer, the term of this patent is extended or adjusted under 35 U.S.C. 154(b) by 309 days.

(21) Appl. No.: 10/429,505

(22) Filed: May 5, 2003

(65) Prior Publication Data

US 2003/0186187 A1 Oct. 2, 2003

Related U.S. Application Data

(63) Continuation of application No. PCT/IB01/02111, filed on Nov. 9, 2001.

(30) Foreign Application Priority Data

Nov. 13, 2000 (EP) ................................. 00811067

(51) Int. Cl.
*A61C 3/00* (2006.01)

(52) U.S. Cl. ...................................................... 433/75
(58) Field of Classification Search .................. 433/75, 433/76, 180, 181, 182; 606/96; 623/17.17
See application file for complete search history.

(56) References Cited

U.S. PATENT DOCUMENTS

| 1,189,753 | A | * | 7/1916 | Thue | 433/76 |
| 5,302,122 | A | * | 4/1994 | Milne | 433/76 |
| 5,350,297 | A | * | 9/1994 | Cohen | 433/76 |
| 5,989,025 | A | * | 11/1999 | Conley | 433/76 |
| 5,997,299 | A | * | 12/1999 | Unger | 433/173 |

FOREIGN PATENT DOCUMENTS

| BE | 877735 | 6/1981 |
| WO | WO 94/00073 | 1/1994 |
| WO | WO 97/49351 | 12/1997 |

* cited by examiner

*Primary Examiner*—Todd E. Manahan
(74) *Attorney, Agent, or Firm*—Sturm & Fix LLP

(57) ABSTRACT

The present invention provides a positioning device for setting implanted bearing dental prostheses in the maxillary bone or for bone grafting on the maxillary bone, including positioning interim dentures along two dimensions, a positioning member along the third dimension, structure for fixing the positioning member on the interim dentures in a specific axial position, a linking member provided with an axial nesting surface, matching a nesting surface of the positioning member, with a surface designed to be fixed to a guide element or a prosthetic element.

29 Claims, 2 Drawing Sheets

POSITIONING DEVICE FOR FITTING IMPLANT-SUPPORTED DENTAL PROSTHESES

CROSS REFERENCE TO RELATED APPLICATIONS

This application is a Continuation application of PCT/IB01/02111 filed Nov. 9, 2001, claiming priority of European Application No. 00811067.8 filed Nov. 13, 2000, which are included in their entirety by reference made hereto.

BACKGROUND OF THE INVENTION

1. Field of the Invention

The present invention relates to a positioning device for fitting implant-supported dental prostheses.

2. Description of the Related Art

The concept of implanting artificial roots to replace missing teeth or as abutments for prostheses is known. The dental implants, generally made of titanium, are screwed into the jawbone where, after osseointegration, that is to say "healing" of the bone around the implant, they will serve as stable abutments on which the future prosthetic restorations (crowns, bridges or dentures) will be fixed.

In a patient without any teeth, when the local anatomical conditions are respected, creating a complete bridge supported by implants represents the best alternative to a removable total prosthesis, both from the point of view of comfort and also from the point of view of mastication function or esthetics.

The durability of the implant depends directly on the quality of its connection to the bone in which it is inserted, to obtain sufficient osseointegration, a waiting period of 2 to 6 months, during which the implant must remain protected from any damaging mechanical stress, is generally necessary between the time it is fitted and the time it is loaded.

Paradoxically, it has now been clearly demonstrated that loading of implants on the same day they are inserted (immediate loading) is possible, for example in the case of restoration of toothless jaws with the aid of rigid structures such as complete bridges, without significantly compromising their long-term viability. The reason for this particular feature lies in better stabilization of the individual implants and more uniform distribution of the mechanical stresses by the rigid structure of the complete bridge, not compromising the phenomenon of osseointegration.

However, the creation of a complete bridge supported by implants poses numerous technical problems associated with their correct insertion. Besides the fact that they have to be inserted at precise locations, they also have to be inserted on a strictly parallel axis permitting postoperative insertion of the bridge.

For this reason, the surgical phase is first of all preceded by what is known as a planning phase during which the future prosthesis is made of wax for diagnostic purposes on casts of the patient's jaws. This makes it possible in particular to decide on the number, position and axis of insertion of the future implants. To ensure a logical continuity between this preliminary step and the surgical phase, it is essential to use a transfer device when fitting the implants: the surgical guide. The latter is in the form of a transparent acrylic resin replica of the future prosthetic restoration. Placed in the mouth, on the toothless gum, it is equipped with parallel wells serving for drilling the implant beds at predetermined locations in the jawbone.

Its use is crucial in cases of restoration of toothless jawbones with complete bridges, accompanied by immediate loading, where postoperative insertion of the temporary bridge is possible only if the implants are placed in a strictly parallel arrangement. Moreover, two other parameters must also be respected in such a situation in order to permit correct occlusion (or meshing) of the bridge with the antagonist teeth: the vertical dimension of occlusion (VDO) and the intermaxillary relationship (IMR). The VDO represents the height of the lower region of the face delimited by the lower margin of the nose and the lower margin of the chin. The IMR represents, in the horizontal plane, the position of the lower jaw relative to the upper jaw.

These three references are established, in the subject completely without teeth, either by the morphology of his/her existing prosthesis (prostheses) or by the diagnostic fitting of the teeth during the preliminary phase. It is imperative that these parameters are transposed to the future bridge which will be placed in the mouth as soon as the final implants have been inserted. Failing to do so leads to problems with occlusion of the teeth and to various clinical manifestations (pain, muscle fatigue, poor mastication, etc.) which are generally not tolerated by the patient.

Hitherto, only surgical guides resting on the toothless gum have been used for implant restoration of toothless jaws. Such restorations generally necessitate incision and reclination of a large surface of the gum, thus compromising the peroperative stability of the surgical guide on the mucous support. Moreover, there is presently no method of reliably recording and plotting the VDO and IMR before the operation to permit precise adaptation of the temporary bridge according to these criteria.

The object of the present invention is to remedy this situation at least in part.

BRIEF SUMMARY OF THE INVENTION

To this end, the present invention first relates to a device for positioning implants for fitting implantable dental prostheses in the jawbone as claimed in claim 1.

The main advantage of this device is to afford an absolute bone reference which can be utilized both on the jawbone to be restored and also on the cast of the toothless ridge on which a large part of the preparatory work for the prosthesis is carried out. On the toothless jawbone, the device has the benefit of an exclusively osseous reference. This reference is maintained in the three spatial dimensions by temporary implants which are inserted into the bone at the start of the intervention. These are connected to the surgical guide by positioning members which permit at any time the removal and then exact repositioning of the guide on its supports. This reference remains even after incision of the gum, since the temporary implant, once it has been connected to the positioning member, ensures an exact repositioning of the surgical guide independently of the state of the gum, which no longer comes into consideration in the positioning of the surgical guide.

By virtue of the positioning members, the location of the temporary implants can be transferred, after taking an impression of the toothless ridge and the positioning members, from the patient's jaw to the cast of the toothless gum without ever losing the initial preoperative reference. The VDO and the IMR are thus maintained throughout the intervention and the bridge can thus be easily adapted to the final implants according to the preoperative VDO and IMR.

As postoperative insertion of a rigid structure such as a bridge is possible only if the final implants have been placed in the same axis, it is necessary to drill parallel holes through the surgical guide at the location of the future final implants.

Another advantage of the positioning device according to the present invention lies in the fact that it is used both in the production of the bridge and of the surgical guide, with the result that the same precision is thus guaranteed on the two members.

The attached drawing is a diagrammatic illustration, given by way of example, of an embodiment of the positioning device which is the subject of this invention.

DETAILED DESCRIPTION OF THE INVENTION

Figure 1:
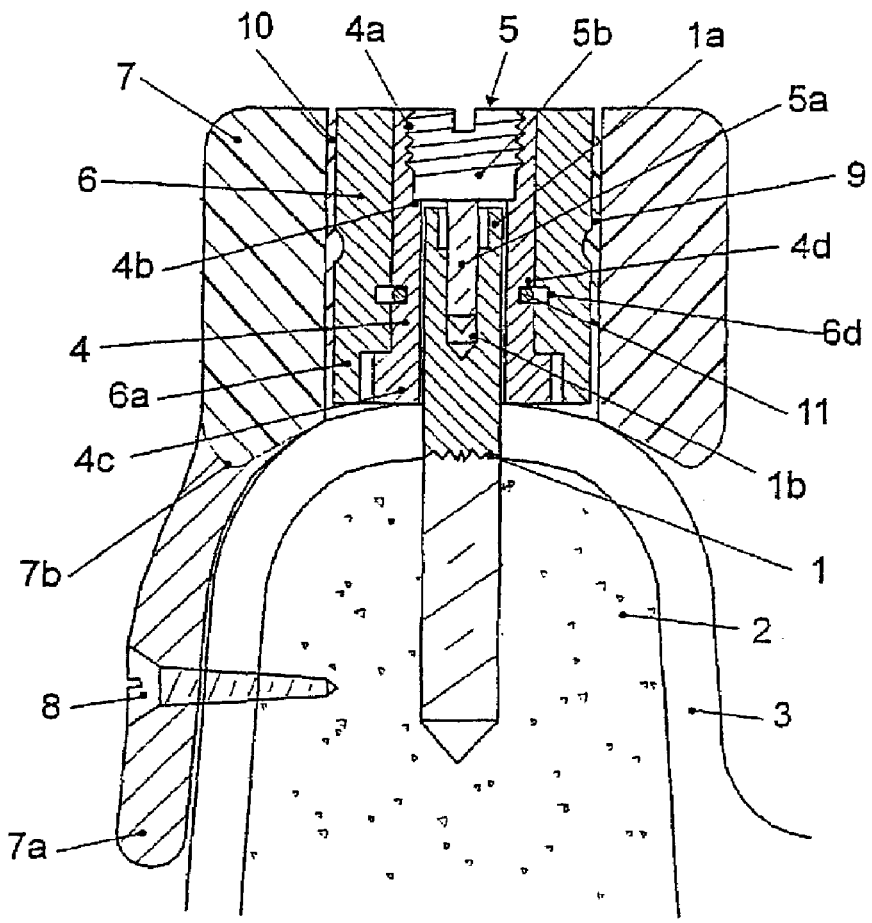
FIG. 1 is an axial section through the positioning device fixed in the jawbone and with a part of the surgical guide.
Figure 2:
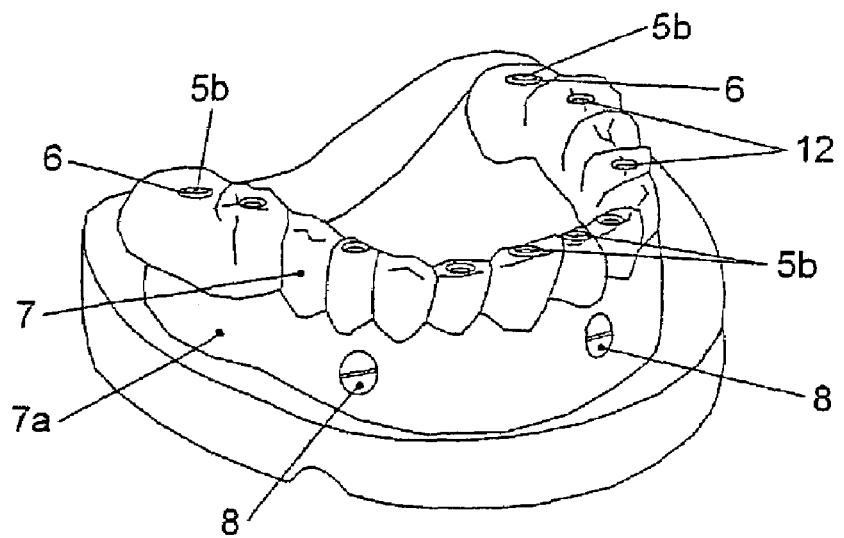
FIG. 2 is a perspective view of the surgical guide arranged on the jaw or the cast of the jaw to be restored.
Figure 3:
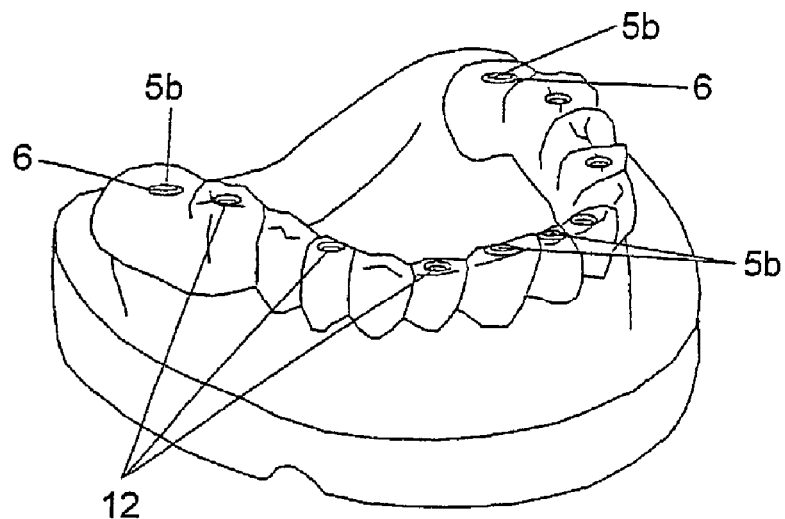
FIG. 3 is another perspective view of the surgical guide after its lateral positioning surface has been removed.

The guide device according to the invention, illustrated in FIG. 1, comprises a temporary implant 1 whose distal part is screwed into the bone of one of the jaws 2 via the gum 3 which covers the latter. This temporary implant 1 constitutes a reference position in two dimensions. The reference position in the third dimension is afforded by a tubular positioning member 4 arranged on the proximal part of the temporary implant 1 protruding from the gum 3. This positioning member 4 is free in relation to the temporary implant 1, that is to say it is not fitted on this temporary implant 1, so that the temporary implant can be freely inserted into the bone by way of the positioning member 4.

The temporary implant 1 consists of a self-tapping screw provided with a cavity 1a at one of its ends, for example of polygonal cross section, to allow a screwing chuck to engage with it so as to connect it to a ratchet handle or micromotor for driving it in rotation. The bottom of the cavity 1a communicates with a threaded blind hole 1b.

The proximal part of the internal surface of the tubular positioning member 4 engaged on that part of the temporary implant 1 emerging from the gum 3 has a larger cross section than the distal part of this internal surface and has a thread 4a. A stabilizing screw 5 comprises two threads, one on its shank 5a in the form of a normal screw, and the other on its head 5b. The thread of the shank 5a of this stabilizing screw 5 comes into engagement with the thread of the blind hole 1b of the implant 1, and that of its head 5b comes into engagement with the thread 4a of the internal surface of the tubular positioning member 4. When the screw head 5b comes into abutment against the shoulder 4b situated at the bottom of the portion of larger cross section of the proximal part of the internal surface of greater diameter of the tubular positioning member 4, the axial position of this tubular positioning member 4 is defined. It is evident that the outer end of the implant 1 must be situated set back in relation to the shoulder 4b so that the axial position of the positioning member 4 on the implant 1 corresponds to the actual level of the alveolar surface of the gum 3. If this was not the case, the screw head would come into abutment against the end of the implant 1 and would pull the tubular positioning member 4 toward it until its shoulder 4b meets the screw head 5b, thus no longer affording the desired reference.

The base of the tubular positioning member 4 ends in an annular abutment 4c on which a tubular connecting member 6 bears whose internal face is designed to match the external lateral face of the tubular positioning member 4, permitting axial engagement and positioning of the tubular connecting member 6 on the tubular positioning member 4. The diameter of the annular abutment 4c is preferably substantially smaller than the external diameter of the tubular connecting member 6 and is lodged inside a thinner annular wall 6a formed at the base of this connecting member 6.

To keep the positioning member 4 engaged axially in the connecting member in the phases preceding its fixation on the temporary implant 1, it is possible to provide an elastic holding mechanism, for example in the form of two annular grooves 4d, 6d formed opposite one another within the cylindrical engagement surfaces of the tubular positioning member 4 and of the connecting member 6, respectively. A spring wire 10 of the piano string type, shaped as a noncircular slotted ring, is lodged in these annular grooves 4d, 6d, passing from one to the other of these annular grooves 4d, 6d, thus preventing axial separation of the engaged components 4 and 6. When a sufficient axial force is exerted with a view to separating these two engaged components 4 and 6, the spring is deformed and lodges in one or other of the annular grooves 4d, 6d, thus permitting axial separation of these two components 4, 6.

The positioning device according to the invention having been described, we will now explain the method of using this device. The surgical guide 7 is made of acrylic resin based on the model of the future prosthesis, itself made on a cast of the toothless jaw to be restored. The surgical guide 7 is equipped with parallel openings 12 intended for the fitting of the final implants (not shown) and also the tubular connecting members 6 to which the positioning members 4 are connected. The tubular connecting members 6 are fixed in the openings of the surgical guide 7 by liquid resin 10 which sets quickly at low temperature. This resin can for example be methyl methacrylate or epoxy resin. Given the presence of the wall 6a surrounding the axial abutment 4c of the tubular positioning member 4, the liquid resin 10 introduced between the connecting member 6 and the opening formed through the surgical guide 7 does not risk accidentally bonding the tubular positioning member 4 to the surgical guide 7. The bore of the positioning member 4 serves to guide the drill bit intended for screwing the temporary implant 1.

The surgical guide 7 (FIG. 1) comprises a vestibular band 7a whose internal face matches the shape of the bone contour so that this vestibular band 7a permits precise positioning of the surgical guide 7 on the jaw.

The surgical guide 7 having the same anatomy as the future bridge, one commences by fixing it temporarily, in the position of occlusion of the jaws, to the jawbone to be restored with the aid of three or four self-tapping screws 8 which are screwed into the jawbone through the vestibular band 7a of the surgical guide 7. This initial stabilization of the guide in the position of occlusion of the jaws guarantees that the fitting of the future final implants takes place according to the VDO and IMR which were chosen before the intervention. The bone is then drilled by way of the bores in the positioning members 4 of the surgical guide 7, at the locations intended to receive the temporary implants 1. The number of these temporary implants 1 is three or four. In the case of a complete restoration of a toothless jaw, two temporary implants 1 can be placed in the molar region, and the other one or other ones can be arranged in the incisor/canine region at the locations left free by the locations intended for the final implants.

After the temporary implants 1 have been screwed in so that they protrude by the desired length and are thus situated at a distance from the top of the gum less than the shoulder 4b of the tubular positioning member 4, a stabilizing screw 5 is screwed into the temporary implant 1 and into the positioning member 4 until the screw head 5b meets the shoulder 4b.

The fact that the diameter of the annular abutment 4c is substantially smaller than the external diameter of the tubular connecting member 6 means it is possible to ensure that the resin 10 introduced between the connecting member 6 and the surgical guide 7 does not bind the latter to the positioning member 4. Consequently, once the screws 5 have been inserted, the temporary screws 8 can be unscrewed from the jaw and the surgical guide 7 can be removed.

Starting from this step, the vestibular part 7a of the surgical guide 7 is removed as far as the dashed lines 7b so as to allow the surgical guide 7 to be replaced on the guide devices, by engaging the internal surfaces of the connecting members 6 integral with the surgical guide 7 on the respective tubular positioning members 4.

Meanwhile, the gum 3 will have been incised and detached from the jawbone, but the surgical guide recovers its initial position by virtue of the positioning devices according to the invention.

The temporary bridge (not shown) which will be fixed on the final implants at the end of the intervention is a replica, made of an esthetic resin, of the surgical guide 7. These two devices, which are produced during the preparatory phase, have identical positioning members 4 and connecting members 6 placed at the same locations. Being interchangeable for this reason, the temporary bridge can be directly fitted to the final implants on the postoperative cast of the restored jaw, in accordance with the preoperative VDO and IMR. This cast is made by taking a simultaneous impression of the final implants and of the temporary implants 1 connected to the positioning members 4 by the stabilizing screws.

The positioning member 4 and the connecting member 6 can be made of metal or of a hard resin. The temporary implant 1 can be made of stainless steel or titanium.

Figure 4:
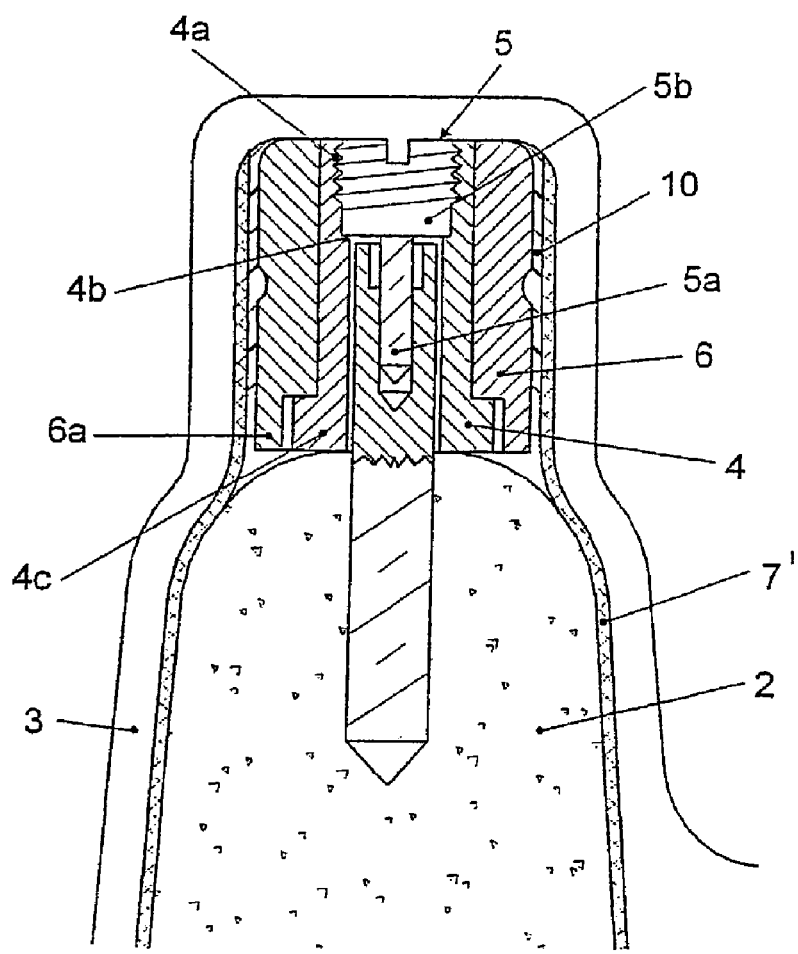
FIG. 4 is an alternative to FIG. 1 illustrating an application of the device according to the invention in the case of a bone graft on a jaw.

In an alternative illustrated in FIG. 4, the device according to the invention is used to perform a bone graft on a jaw, in a phase preliminary to its restoration. In this alternative, the surgical guide is replaced by a retention grating 7' made of titanium or stainless steel and intended to position and maintain the grafted bone on the jaw. The positioning device according to the invention makes it possible to precisely determine the position of the retention grating 7' relative to the jaw on which the bone is grafted. During the period in which the bone graft takes, the retention grating 7' is covered by the gum 3.

What is claimed is:

1. A positioning device for fitting implant-supported dental prostheses in the jawbone or for grafting on the jawbone of a toothless jaw to be restored, the positioning device comprising:
    a guide element or a prosthetic element having a surface fitting the toothless jaw to be restored narrowly and solid with connecting members each provided with an axial engagement internal surface;
    positioning members each having an axial engagement external surface matching the axial engagement internal surface of one of said connecting members, and an axial drilling positioning bore for positioning a temporary implant in two dimensions; and
    means for fixing said positioning members on the temporary implants in a determined third axial dimension, so that said connecting members may be axially connected to, and respectively disconnected from said positioning members, whereas the positioning members are fixed on the temporary implants.

2. The positioning device as claimed in claim 1, wherein each of said positioning members is a tubular member whose internal surface is engaged on the proximal end of said temporary implant and whose external surface forms an engagement surface, the cross section of the proximal portion formed by said internal surface being larger than that of its distal portion and being provided with a thread, wherein an axial abutment is integral with said engagement surface, wherein said connecting member is a tubular member whose internal surface matches said engagement surface of said positioning member, and wherein said fixing means comprise a screw with a head having two threaded portions, one integral with the shank of the screw and disposed to be screwed into said temporary implant, the other integral with its head and disposed to engage with the thread of said proximal portion of said positioning member in order to fix the axial position of the positioning member in relation to said implant when said screw head, engaging with the thread of said proximal portion, abuts against the shoulder formed between this proximal portion of larger diameter and the portion of smaller diameter.

3. The device as claimed in claim 2 wherein the fixing means of said temporary implant is formed by a self-tapping screw whose outer end has a cavity configured to allow a screwing chuck to engage with it and whose bottom communicates with an internal thread in order to receive a stabilizing screw.

4. The positioning device as claimed in claim 3 wherein said surface of said connecting member disposed to be fixed to a guide element or to a prosthetic element is configured to improve the fastening, with a binder, of the connecting member to said guide or to said prosthesis.

5. The positioning device as claimed in claim 2 wherein said surface of said connecting member disposed to be fixed to a guide element or to a prosthetic element is configured to improve the fastening, with a binder, of the connecting member to said guide or to said prosthesis.

6. The positioning device as claimed in claim 2 wherein said guide member is a surgical guide for determining the respective positions of final implants.

7. The positioning device as claimed in claim 2 wherein said guide member is a retaining member for performing a bone graft on a jawbone.

8. The positioning device as claimed in claim 2, further including an elastic holding member arranged between the matching engagement surfaces of said positioning member and of said connecting member.

9. The device as claimed in claim 1 wherein the fixing means of said temporary implant is formed by a self-tapping screw whose outer end has a cavity configured to allow a screwing chuck to engage with it and whose bottom communicates with an internal thread in order to receive a stabilizing screw.

10. The positioning device as claimed in claim 9 wherein said surface of said connecting member disposed to be fixed to a guide element or to a prosthetic element is configured to improve the fastening, with a binder, of the connecting member to said guide or to said prosthesis.

11. The positioning device as claimed in claim 9 wherein said guide member is a surgical guide for determining the respective positions of final implants.

12. The positioning device as claimed in claim 9 wherein said guide member is a retaining member for performing a bone graft on a jawbone.

13. The positioning device as claimed in claim 9, further including an elastic holding member arranged between the matching engagement surfaces of said positioning member and of said connecting member.

14. The positioning device as claimed in claim 1 wherein said surface of said connecting member disposed to be fixed to a guide element or to a prosthetic element is configured to improve the fastening, with a binder, of the connecting member to said guide or to said prosthesis.

15. The positioning device as claimed in claim 14 wherein said guide member is a surgical guide for determining the respective positions of final implants.

16. The positioning device as claimed in claim 14 wherein said guide member is a retaining member for performing a bone graft on a jawbone.

17. The positioning device as claimed in claim 14, further including an elastic holding member arranged between the matching engagement surfaces of said positioning member and of said connecting member.

18. The positioning device as claimed in claim 1 wherein said guide member is a surgical guide for determining the respective positions of final implants.

19. The positioning device as claimed in claim 18 wherein said guide member is a retaining member for performing a bone graft on a jawbone.

20. The positioning device as claimed in claim 18, further including an elastic holding member arranged between the matching engagement surfaces of said positioning member and of said connecting member.

21. The positioning device as claimed in claim 1 wherein said guide member is a retaining member for performing a bone graft on a jawbone.

22. The positioning device as claimed in claim 21, further including an elastic holding member arranged between the matching engagement surfaces of said positioning member and of said connecting member.

23. The positioning device as claimed in claim 1, further including an elastic holding member arranged between the matching engagement surfaces of said positioning member and of said connecting member.

24. A positioning device for fitting implant-supported dental prostheses in the jawbone or for grafting on the jawbone, the positioning device comprising:
   temporary implants for positioning in two dimensions;
   a positioning member for positioning in a third dimension;
   means for fixing said positioning member on the temporary implants in a determined axial position;
   connecting member provided with an axial engagement surface matching an engagement surface of said positioning member, and provided with a surface disposed to be fixed to a guide element or a prosthetic element, wherein said positioning member is a tubular member whose internal surface is engaged on the proximal end of said temporary implant and whose external surface forms an engagement surface, the cross section of the proximal portion formed by said internal surface being larger than that of its distal portion and being provided with a thread, wherein an axial abutment is integral with said engagement surface, wherein said connecting member is a tubular member whose internal surface matches said engagement surface of said positioning member, and wherein said fixing means comprise a screw with a head having two threaded portions, one integral with the shank of the screw and disposed to be screwed into said temporary implant, the other integral with its head and disposed to engage with the thread of said proximal portion of said positioning member in order to fix the axial position of the positioning member in relation to said implant when said screw head, engaging with the thread of said proximal portion, abuts against the shoulder formed between this proximal portion of larger diameter and the portion of smaller diameter.

25. The device as claimed in claim 24 wherein the fixing means of said temporary implant is formed by a self-tapping screw whose outer end has a cavity configured to allow a screwing chuck to engage with it and whose bottom communicates with an internal thread in order to receive a stabilizing screw.

26. The positioning device as claimed in claim 24 wherein said surface of said connecting member disposed to be fixed to a guide element or to a prosthetic element is configured to improve the fastening, with a binder, of the connecting member to said guide or to said prosthesis.

27. The positioning device as claimed in claim 24 wherein said guide member is a surgical guide for determining the respective positions of final implants.

28. The positioning device as claimed in claim 24 wherein said guide member is a retaining member for performing a bone graft on a jawbone.

29. The positioning device as claimed in claim 24, further including an elastic holding member arranged between the matching engagement surfaces of said positioning member and of said connecting member.

* * * * *